United States Patent [19]

Beliveau

[11] Patent Number: 5,038,989
[45] Date of Patent: Aug. 13, 1991

[54] APPARATUS FOR PARTIALLY SLITTING ABSORBENT BOARDS

[75] Inventor: Jean-Marc Beliveau, Ville d'Anjou, Canada

[73] Assignee: Johnson & Johnson Inc., Montreal, Canada

[21] Appl. No.: 242,274

[22] Filed: Sep. 12, 1988

[51] Int. Cl.5 ............................................. D01D 5/42
[52] U.S. Cl. ........................................ 225/93; 225/97
[58] Field of Search ............................... 225/3, 93, 97; 28/DIG. 1; 57/DIG. 907; 264/DIG. 8, 146; 83/660, 861, 120

[56] References Cited

U.S. PATENT DOCUMENTS

| 2,609,049 | 9/1952 | Rayburn | 225/3 |
| 2,621,622 | 12/1952 | Henchert | 225/3 |
| 3,035,497 | 5/1962 | Whitehead et al. | 225/93 |
| 3,156,016 | 11/1964 | Dunlap et al. | 19/66 T |
| 3,518,921 | 7/1970 | Muller | 83/660 |
| 3,577,724 | 5/1971 | Greene | 225/3 |
| 3,679,111 | 7/1972 | Volans | 225/97 |
| 3,939,744 | 2/1976 | Junker | 83/122 |
| 4,459,888 | 7/1984 | Frye | 83/51 |
| 4,635,316 | 1/1987 | Towne et al. | 83/660 |

Primary Examiner—Hien H. Phan
Attorney, Agent, or Firm—Joseph F. Shirtz

[57] ABSTRACT

Apparatus having two spaced rolls with a plurality of intermeshed disc-like teeth. The rolls form a nip into which an absorbent board is fed for partial slitting. The board is comprised of both long and short fibers. The apparatus separates the short fibers at each slit while leaving a number of long fibers intact to maintain a unitary structure. Advantageously, the teeth of one roll form gaps slightly wider than the thickness of the long fibers with the teeth of the other roll to permit passage of the long fibers.

2 Claims, 4 Drawing Sheets

APPARATUS FOR PARTIALLY SLITTING ABSORBENT BOARDS

This application is related to commonly assigned, co-pending patent application Ser. No. 242,271, filed Sept. 12, 1988, now U.S. Pat. No. 4,992,326, and entitled "Flexible Absorbent Board".

FIELD OF THE INVENTION

This invention relates to apparatus useful in modifying absorbent material for products such as sanitary napkins, diapers, tampons and the like, and more particularly in partially slitting an absorbent board to provide flexibility to the board while maintaining a unitary product.

BACKGROUND OF THE INVENTION

Absorbent materials in the form of relatively dense sheet-like structures resembling heavy weight paper, blotter paper or paperboard are referred to as absorbent boards. This terminology distinguishes such absorbents from loose, bulky materials such as wood pulp, fluff and the like. Absorbent boards may be formed of a variety of materials of natural and/or synthetic origin. For example, absorbent boards may be prepared from wood pulp, peat moss and mixtures thereof, optionally including other components such as reinforcing synthetic textile fibers, natural fibers, binders, surfactants and the like. Such boards are commonly prepared by wet laying a slurry of the solid components of the board on conventional papermaking equipment.

For example, U.S. Pat. No. 4,507,122 discloses a laminate structure comprising a thin layer of kraft paper and a heavier layer of a mixture of peat moss and wood pulp. The materials are sequentially deposited from an aqueous slurry in a wet process on conventional paper making equipment. The deposited solids are dewatered, partially dried and compressed to a density from about 0.2 to 1.0 g/cc. The resulting absorbent board is relatively stiff, and flexibility may be increased by mechanical working such as embossing microcreping or microcorrugating. The reference suggests that the flexibility of the board may also be increased by slitting.

The present invention is concerned with a novel apparatus for improvement of an absorbent structure composed of peat moss, wood pulp, mixtures thereof or other compacted friable absorbent material. The apparatus provides increased flexibility in at least one direction to absorbent boards.

SUMMARY OF THE INVENTION

The apparatus conveniently works to partially slit absorbent boards to provide flexibility with structural integrity. The boards are formed of a mixture of long fibers and short fibers. The apparatus has a pair of parallel rolls having circumferential, disc-like teeth. The teeth of one roll are slightly offset from the teeth of the other roll. The rolls are positioned to form a nip therebetween into which the absorbent board is fed.

The teeth are advantageously shaped to displace longitudinal portions of the board out of the plane of the board while preventing displacement of adjacent portions thus tearing the board to form longitudinal slits. The tearing separates the short fibers of the board but leaves many of the long fibers intact and extending between adjacent longitudinal board portions.

The teeth of the rolls are laid out in a saw-tooth pattern. Each tooth is formed of a first circumferential surface which is perpendicular to the roll axis and a second circumferential surface at an angle to the roll axis. The two surfaces meet to form a tooth apex.

The rolls are positioned so the perpendicular surface of each of the teeth of one roll faces the perpendicular surface of an adjacent tooth on the other roll. Likewise, the other surface of each tooth faces and is spaced from a corresponding surface of a tooth on the other roll. Thus, a plurality of pockets are formed which have offset edges.

In order to prevent the absorbent board from wrapping around one of the rolls, a pair of doctor blades are provided. The doctor blades each have a leading edge which is disposed close to the surface of one or the other of the rolls. The edge can be shaped to fit the roll and closely follow its surface. The doctor blades extend at an acute angle to the plane of the absorbent board at the point where the board exits the nip of the roll.

The absorbent structure fed into the apparatus is preferably composed of peat moss and is formed as a board by air or wet laying and calendering to obtain a relatively thin, i.e. from about 0.01 to 0.05 inch thick, relatively dense, i.e. from about 0.2 to 1.0 g/cc sheet-like structure. The structure may include a layer of kraft tissue laminated on one or both surfaces of the peat moss layer. The absorbent board thus formed is a relatively thin but stiff structure similar to those described in the above-described reference.

As used herein "partially slit" means to cut, separate or tear the short fibers of the peat moss or wood pulp while leaving intact a number of longer staple fibers. The fibers which remain intact, bridge the slit formed by the cutting, separating or tearing of the structure to provide integrity to the unit.

BRIEF DESCRIPTION OF THE DRAWINGS

The apparatus will now be described in detail with reference to the accompanying figures wherein.

DETAILED DESCRIPTION OF THE INVENTION

Figure 1:
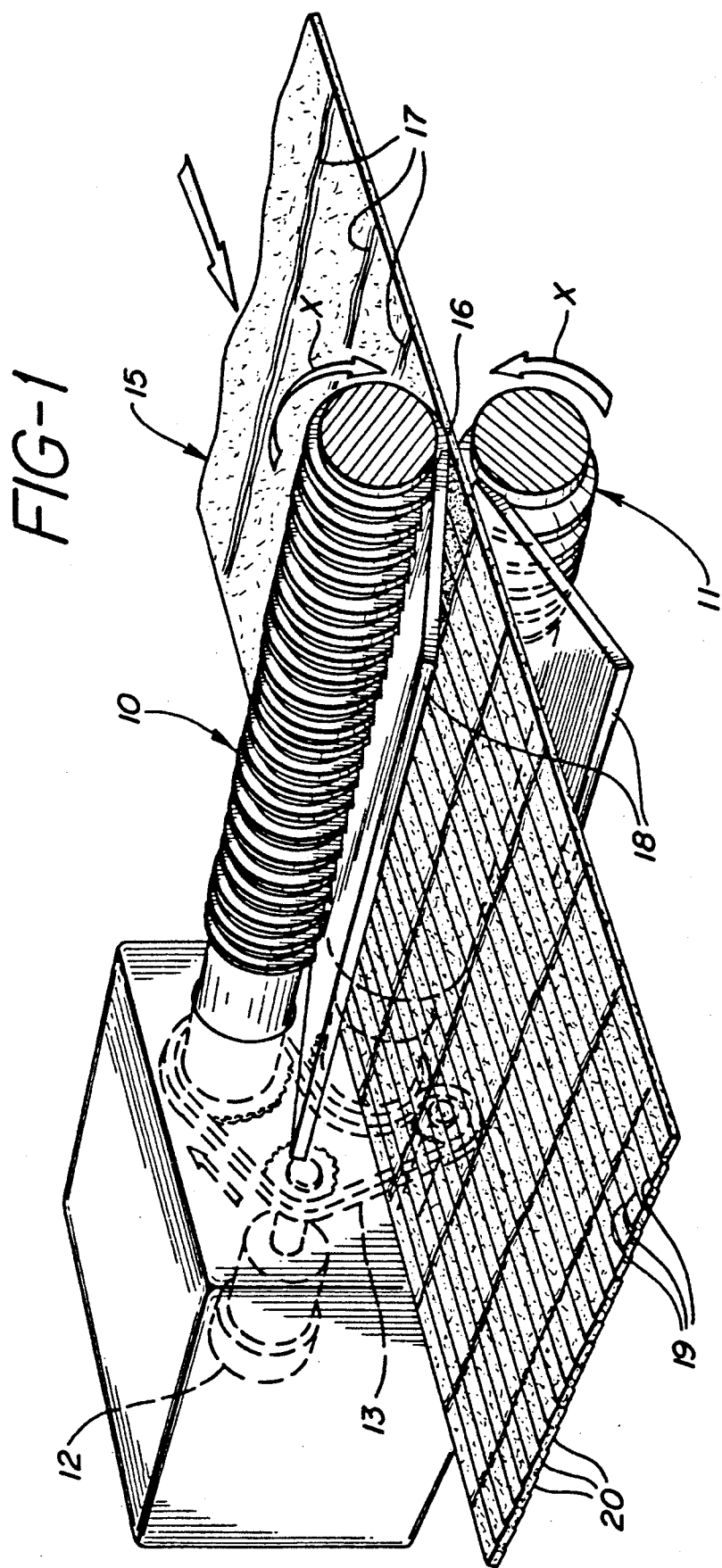
FIG. 1 is a partial perspective view of the apparatus of the invention.

Referring now to FIG. 1, a pair of spaced rolls 10,11 are positioned with their longitudinal axes parallel to each other. The rolls are driven in opposite directions as indicated by arrows X. The rolls may be driven in any suitable manner, for example, an electric motor 12 may drive an endless belt 13. The belt 13 travels a serpentine path about pulleys 14 to provide the opposite rotation of the rolls. Alternatively, the belt 13 may be replaced by a chain which drives sprockets to rotate the rolls.

An absorbent board 15 is fed into the nip 16 of rolls 10,11. The board 15 may have spaced embossments 17 extending transversely of board 15. Embossments 17 provide additional flexibility to the board about an axis parallel to the embossments 17 after slitting, a pair of doctor blades 18 assists the removal of the slit board from the nip 16.

Figure 2:
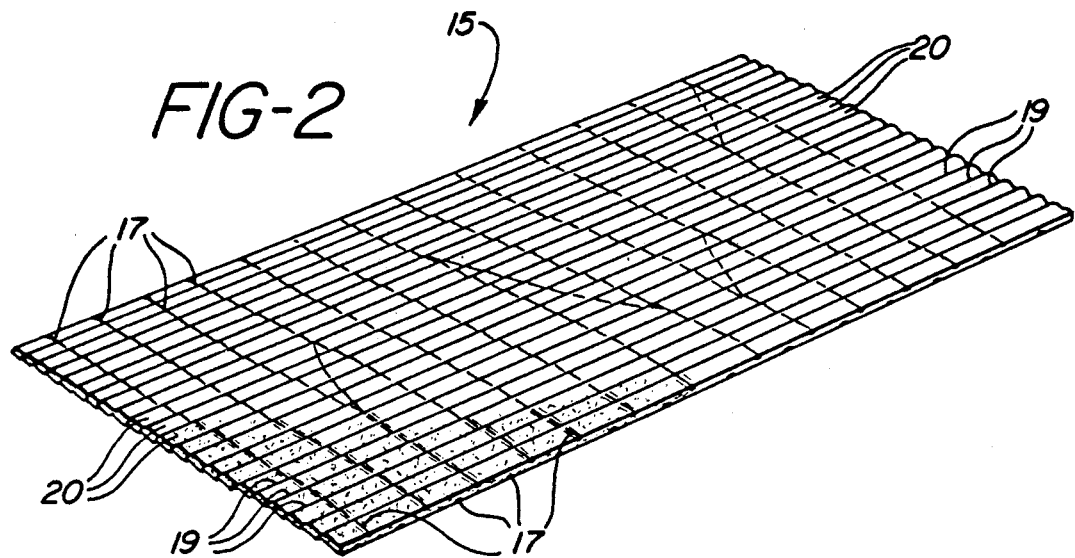
FIG. 2 is a perspective view of an absorbent board after slitting by the apparatus.
Figure 3:
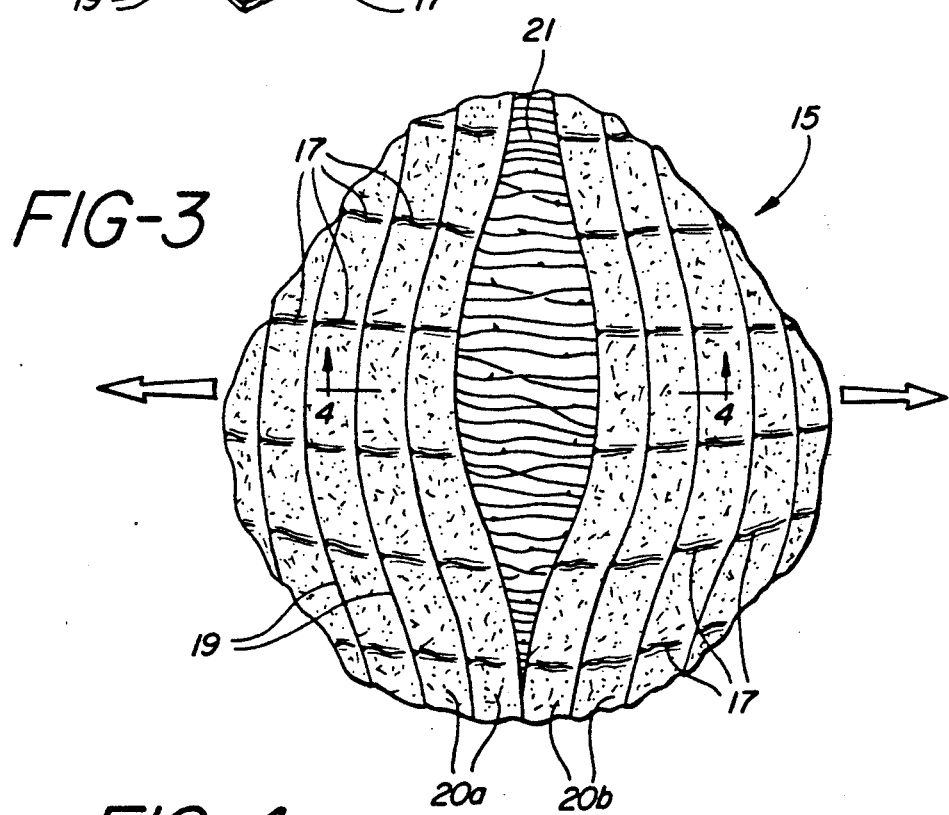
FIG. 3 is an enlarged view of a portion of the slit absorbent board with adjacent board portions pulled apart.
Figure 4:
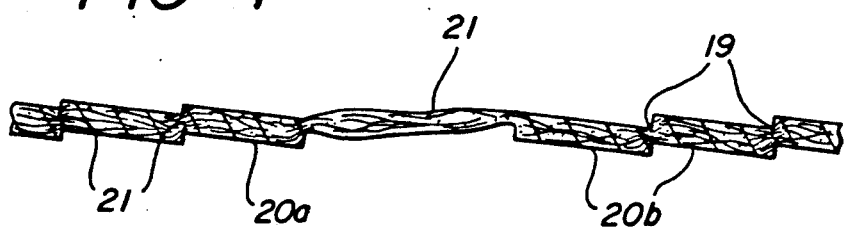
FIG. 4 is a cross-sectional view of FIG. 3 along line 4—4.

After treatment by the rolls 10,11, the board 15 appears as shown in FIG. 2. The board has slits 19 extending longitudinally through the board. The slits 19 partially separate strip-like portions 20. As seen more clearly in FIG. 3, the strip-like portions are interconnected by longer fibers 21 in the board. In FIGS. 3 and 4, the slit 19 is shown in a condition in which adjacent strip-like portions 20a, 20b are pulled apart. The strip-like portions are substantially discrete sections. However, in order to maintain the integrity of the board, fibers 21 extend between adjacent strip-like portions to interconnect them. In cross-section, the slitted board has a saw-toothed design. The adjacent strip-like portions having been shifted vertically to create the slits without cutting the long fibers which interconnect the adjacent strip-like portions 20a, 20b. However, this saw-toothed design is merely a function of the tooth shape and is not necessarily the shape of the final product.

Figure 5:
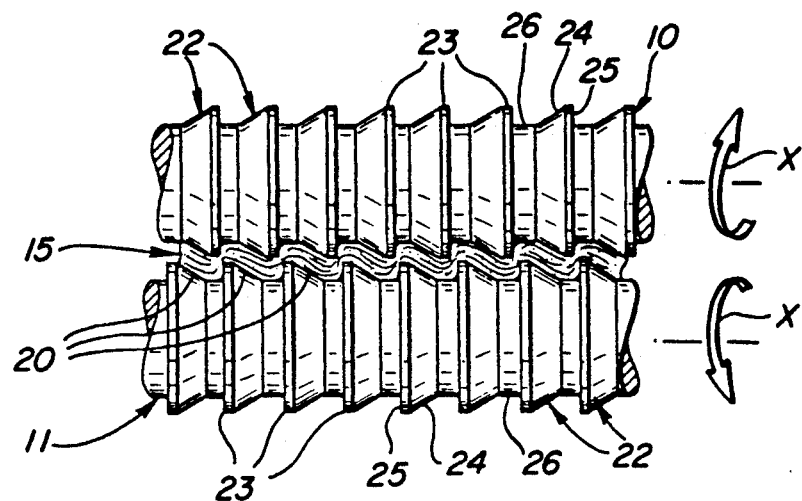
FIG. 5 is a partial end view of the nip of the rolls of one embodiment of the invention.
Figure 6:
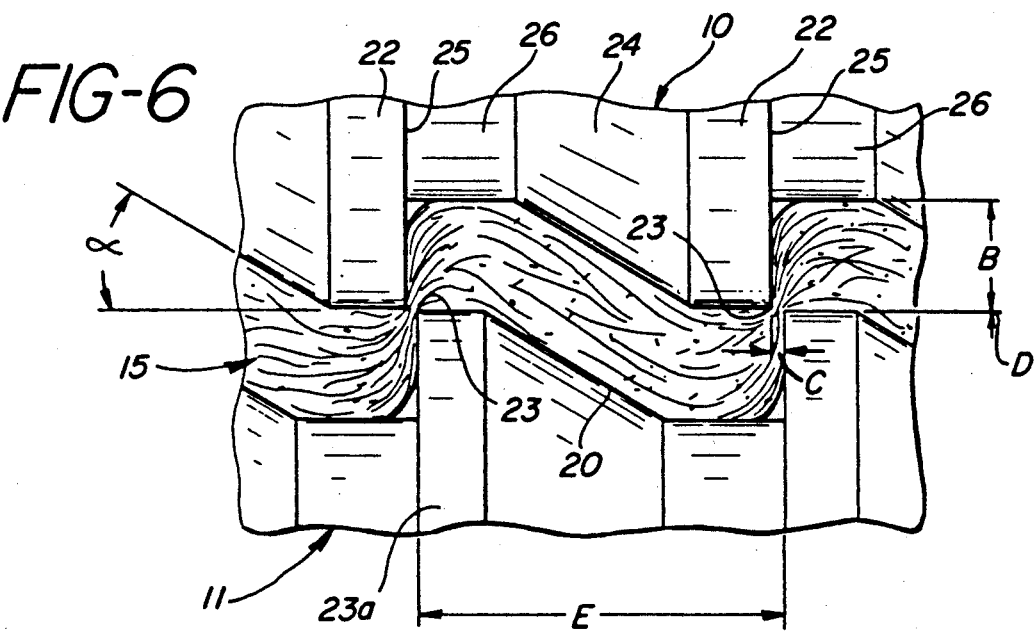
FIG. 6 is an enlarged view of the nip of FIG. 5.

In order to create the slits 19, the rolls 10,11 are provided with an outer circumferential surface as shown in FIG. 5. The surface has circumferential teeth 22 which each form an apex 23 at the juncture of sloped surface 24 and perpendicular surface 25. However, in the preferred embodiment, the teeth have flat lands 23a. The rolls 10,11 have substantially the same tooth shape. However, the rolls are positioned with their axes parallel but extending in opposite directions so the teeth mate longitudinally in a spaced configuration (FIG. 6). Thus, the teeth define a plurality of saw-toothed pockets for the board to pass through.

Perpendicular surface 25 extends substantially perpendicular to the axis of rotation of the rolls. The sloped surface 24, however, forms an angle $\alpha$ with the roll axis. This angle may be approximately 30°. The rolls are preferably positioned so the apex or the flat of the teeth of one roll extend slightly past the plane of the apex or flat of the teeth of the other roll. That is, the separation dimension D in the range of 0.01 inch to minus 0.006 inch. This range is for a 300 g/m² basis weight peat moss board. Different dimensions may be necessary for other products. For thick products, the dimension may even be positive.

The dimensions of the teeth will now be described with respect to slitting a peat moss board having a thickness of about 0.02–0.10 inches. The board has long fibers or fibrous components which are preferably a synthetic fiber such as polyester fiber having a denier of from 1 to 5 and staple length of from 0.5 to 1.5 inches. The polyester fiber is blended with the peat moss and/or wood pulp to form a uniform mixture before forming the board. The polyester fiber is preferably added in an amount equal to from 2 to 20% by weight of the dry components of the absorbent board, and most preferably in an amount from about 4 to 8% by weight The board has a final thickness of approximately 0.015 inch if calendered and about 0.038 inch if microcreped.

The rolls are preferably about two inches in diameter and are positioned so adjacent perpendicular faces are separated by 0.002 inch (dimension "C"). The teeth have a height B of approximately 0.036 inch and a tooth length E of approximately 0.080 inch. These dimensions change depending on the board being slit. Dimension "C" is generally greater than the size of the long fibers plus 0.0015 inch.

Figure 7:
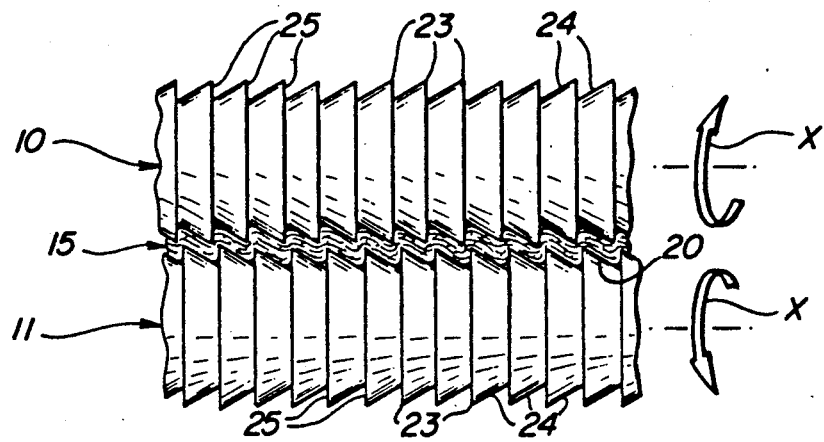
FIG. 7 is a partial end view of the nip of the rolls of an alternate embodiment of the invention.
Figure 8:
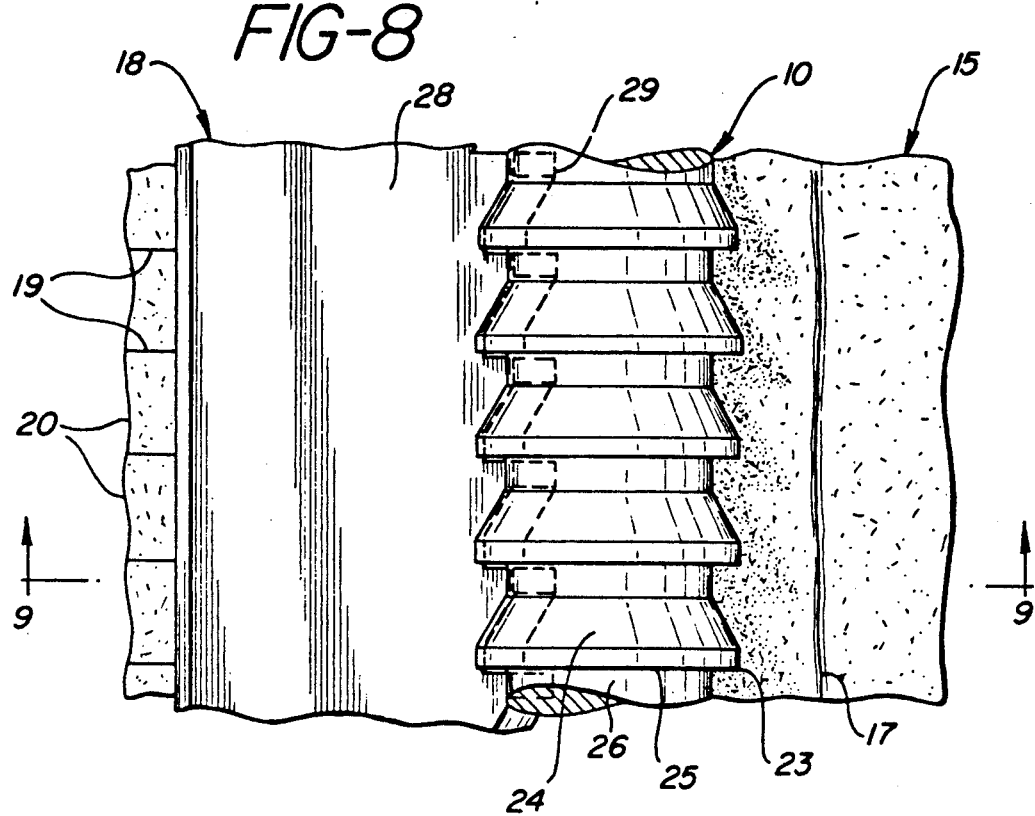
FIG. 8 is a partial top elevation of the rolls and doctor blade.
Figure 9:
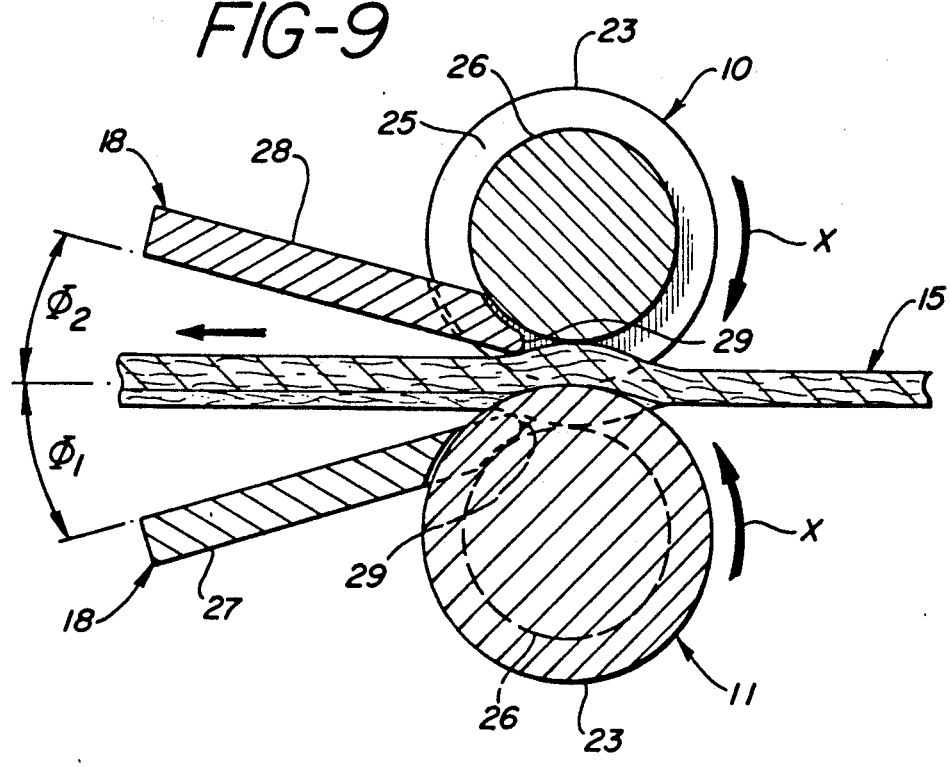
FIG. 9 is a cross-section along line 9—9 of FIG. 8.

The embodiment shown in FIGS. 5 and 6 has flat lands 26 which permit a wider distance between slits without greatly disturbing the tooth dimensions. The lands 26 mate with flats 23a of the opposing roll to give support to adjacent board portions as the slit is formed. The lands 26 may be eliminated as in FIG. 7 in which case rolls having the dimensions described above would have a tooth length of 0.063 inch.

In order to guide the slit board out of the roller nip 16, a pair of doctor blades 27,28 are provided. The doctor blades have a leading edge 29 which closely follows the surface shape of the rolls. The lower blade 27 forms an angle $\Phi_1$, of 5° with the plane of the material. The upper blade 28 forms an angle $\Phi_2$ of 15° with the plane of the material.

In operation, an absorbent board 15 is fed into the nip 16 of the rolls 10,11. In the nip, adjacent board portions are separated by sloped surface 24 pushing one edge of the portion 20a in one direction out of the plane of the board while the sloped surface of an adjacent tooth on the opposite roll pushes the adjacent edge of the adjacent portion 20b in the opposite direction out of the plane of the board. Thus, each adjacent portion is twisted slightly in the same direction, tearing open the slits. The gap between the teeth of opposing rolls, however, permits the long fibers to pass unsevered. The board may stick to the roll's surface or may delaminate if the board is not guided off the roll surface. Therefore, the doctor blades gently guide the board off the rolls and direct it for further processing.

The invention has been described with reference to its preferred embodiment and preferred board construction. However, variations to this embodiment may be made while remaining within the spirit of the invention.

What is claimed is:

1. An apparatus for partially slitting an absorbent board comprising:
    (a) a pair of spaced parallel rolls having longitudinal axes, mounted for rotation about said axes;
    (b) circumferential surfaces on each of said rolls which mate with the circumferential surface of the other roll to form a nip between said rolls;
    (c) means for rotating said rolls to pull said absorbent board through said nip;
    (d) slitting means on said circumferential surfaces which displace portions of said absorbent board at least partially out of the plane of said board as said rolls rotate to move said board through said nip, said slitting means including:
        (i) a plurality of circumferential teeth on each roll which are offset from similar teeth on the other roll, said teeth having a pair of surfaces forming a circumferential ape which displaces a portion of the absorbent board in a direction away from the axis of the roll as an adjacent tooth on the other roll prevents movement of an adjacent portion of the absorbent board in the same direction, partially tearing a slit between the two adjacent portion, a first of said pair of surfaces being perpendicular to the axis of the roll and the second surface forms an angle of less than 90° with the axis; and, (ii) a flat longitudinal surface extending between said two circumferentially extending surfaces at a point radially below the apexes of the teeth formed in part by the surfaces said flat longitudinal surface extends between.

2. An apparatus for partially slitting an absorbent board made from a mixture of short and long fibers comprising:
   (a) a pair of spaced parallel rolls having longitudinal axes mounted for rotation about said axes;
   (b) circumferential surfaces on each of said rolls which mate with the circumferential surfaces of the other roll to form a nip between said rolls;
   (c) slitting means on said circumferential surfaces which displace portions of said absorbent board and at least partially out of the plane of said board to tear the short fibers of the board as said rolls rotate to move said board through said nip and having a gap large enough to permit passage of long fibers without severing all of the long fibers, said slitting means comprising:
      (i) a plurality of circumferential teeth on each roll which are offset from similar teeth on the other roll, said teeth having a pair of surfaces forming a circumferential apex which displaces a portion of the absorbent board in a direction away from the axis of the roll as an adjacent tooth on the other roll prevents movement of an adjacent portion of the absorbent board in the same direction, partially tearing a slit between the two adjacent portions;
      (ii) each of said teeth is shaped with two circumferentially extending surfaces which meet to form the apex, a first surface is perpendicular to the axis of the roll and the second surface forms an angle of less than 90° with the axis;
      (iii) a flat longitudinal surface extending between said two circumferentially extending surfaces at a point radially below the apexes of the teeth formed in part by the surfaces of said flat longitudinal surface extends between; and
   (d) means for rotating said rolls to pull said absorbent board through said nip.

* * * * *

UNITED STATES PATENT AND TRADEMARK OFFICE
CERTIFICATE OF CORRECTION

PATENT NO. : 5,038,989
DATED : August 13, 1991
INVENTOR(S) : Jean-Marc Beliveau

It is certified that error appears in the above-identified patent and that said Letters Patent is hereby corrected as shown below:

In Claim 1, Column 4, Line 59: "ape" should be --apex--.

In Claim 1, Column 4, Line 65: "portion" should be --portions--.

Signed and Sealed this

Twenty-third Day of February, 1993

Attest:

STEPHEN G. KUNIN

*Attesting Officer*     *Acting Commissioner of Patents and Trademarks*